(12) United States Patent
Regensburger et al.

(10) Patent No.: US 11,793,595 B2
(45) Date of Patent: Oct. 24, 2023

(54) THERAPEUTIC APPARATUS FOR ULTRASONIC TREATMENT

(71) Applicant: Siemens Healthcare GmbH, Erlangen (DE)

(72) Inventors: Alois Regensburger, Poxdorf (DE); Tobias Lenich, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 18/099,342

(22) Filed: Jan. 20, 2023

(65) Prior Publication Data

US 2023/0233282 A1    Jul. 27, 2023

(30) Foreign Application Priority Data

Jan. 24, 2022    (DE) .................... 10 2022 200 740.9

(51) Int. Cl.
| | |
|---|---|
| *A61B 90/00* | (2016.01) |
| *A61B 8/06* | (2006.01) |
| *A61B 8/08* | (2006.01) |
| *A61N 7/00* | (2006.01) |
| *A61B 17/22* | (2006.01) |

(52) U.S. Cl.
CPC ................ *A61B 90/37* (2016.02); *A61B 8/06* (2013.01); *A61B 8/5223* (2013.01); *A61N 7/00* (2013.01); *A61B 2017/22008* (2013.01); *A61B 2090/378* (2016.02); *A61N 2007/0039* (2013.01)

(58) Field of Classification Search
CPC .. A61N 7/00; A61B 90/37; A61B 8/06; A61B 8/5223; A61B 2090/378; A61B 2017/22008
See application file for complete search history.

(56) References Cited

U.S. PATENT DOCUMENTS

2004/0138563 A1*  7/2004  Moehring ............... A61B 8/06
                                                              600/439
2007/0083120 A1*  4/2007  Cain .................. A61M 37/0092
                                                              600/439

(Continued)

OTHER PUBLICATIONS

Bader, Kenneth B., Eli Vlaisavljevich, and Adam D. Maxwell. "For whom the bubble grows: physical principles of bubble nucleation and dynamics in histotripsy ultrasound therapy." Ultrasound in medicine & biology 45.5 (2019): 1056-1080.

(Continued)

*Primary Examiner* — John Denny Li
(74) *Attorney, Agent, or Firm* — Lempia Summerfield Katz LLC

(57) ABSTRACT

A therapeutic apparatus for therapeutic ultrasonic treatment of a tissue region that contains a flowing liquid has at least one ultrasonic source and a control unit for activating the ultrasonic source in order to radiate ultrasonic pulses according to a pulse parameter set into the tissue region. The therapeutic apparatus has a measuring system configured to determine a flow velocity of the liquid and a focus control system configured to move a focus region of the ultrasonic pulse relative to the tissue region over a longitudinal portion. A movement direction of the focus region therein corresponds to a flow direction of the liquid and a movement velocity of the focus region corresponds to the flow velocity.

14 Claims, 1 Drawing Sheet

1 Therapeutic apparatus
2 Vessel
3 Patient
4 Ultrasonic source
5 Focus control system
6 Control unit
7 Measuring system
8 Focus region

(56) References Cited

U.S. PATENT DOCUMENTS

| | | | | |
|---|---|---|---|---|
| 2007/0161897 A1* | 7/2007 | Sasaki | ............... | A61N 7/02 |
| | | | | 600/439 |
| 2010/0274130 A1* | 10/2010 | Anand | ............... | A61N 7/02 |
| | | | | 600/439 |
| 2011/0118600 A1* | 5/2011 | Gertner | ............... | A61B 6/032 |
| | | | | 601/2 |
| 2018/0064412 A1* | 3/2018 | Messas | ............... | A61B 8/0883 |
| 2019/0216478 A1 | 7/2019 | Maxwell et al. | | |
| 2019/0329075 A1* | 10/2019 | Sutton | ............... | A61B 5/0036 |
| 2021/0196295 A1* | 7/2021 | Goudot | ............... | A61N 7/00 |

OTHER PUBLICATIONS

Decision to Grant for German Application No. 10 2022 200 740.9, decision dated Oct. 17, 2022, with English Translation.

German Office Action for Germany Application No. 10 2022 200 740.9 dated Jun. 15, 2022, with English Translation.

Ohl, Siew-Wan, Evert Klaseboer, and Boo Cheong Khoo "Bubbles with shock waves and ultrasound: a review." Interface focus 5.5 (2015): 20150019. pp. 1-15.

Qu, Shibin, et al. "Non-thermal histotripsy tumor ablation promotes abscopal immune responses that enhance cancer immunotherapy." Journal for immunotherapy of cancer 8.1 (2020). pp. 1-12.

* cited by examiner

1 Therapeutic apparatus
2 Vessel
3 Patient
4 Ultrasonic source
5 Focus control system
6 Control unit
7 Measuring system
8 Focus region 2 Vessel
2a Vessel wall
2b Liquid
9 Vessel constriction
10a, 10b Vessel regions

THERAPEUTIC APPARATUS FOR ULTRASONIC TREATMENT

The present patent document claims the benefit of German Patent Application No. 10 2022 200 740.9, filed Jan. 24, 2022, which is hereby incorporated by reference in its entirety.

TECHNICAL FIELD

The present disclosure relates to a therapeutic apparatus for therapeutic ultrasonic treatment of a tissue region which contains a flowing liquid, wherein the therapeutic apparatus has at least one ultrasonic source and at least one control unit configured to activate the at least one ultrasonic source according to a pulse parameter set in order to radiate ultrasonic pulses into the tissue region for therapeutic ultrasonic treatment. The disclosure also relates to a computer program product with commands which, when executed by a therapeutic apparatus, cause the therapeutic apparatus to carry out a method for therapeutic ultrasonic treatment.

BACKGROUND

In order to break down deposits in vessels or on heart valves, or vessel constrictions, also referred to as stenoses, methods for therapeutic ultrasonic treatment such as histotripsy methods may be applied intravascularly. Therein, it may occur, due to body movements, poor focusing ability of the ultrasonic waves or other irregularities that in an undesirable manner, healthy tissue regions are damaged or destroyed.

Histotripsy is a method for therapeutic ultrasonic treatment which may be used, inter alia, for non-invasive tumor ablation, as described, for example, in the publication by Q. Shibin et al. "Non-thermal histotripsy tumor ablation promotes abscopal immune responses that enhance cancer immunotherapy," Journal for ImmunoTherapy of Cancer, 8 (1), 2020, but may also be used intravascularly.

Therein, by way of high-intensity ultrasonic pulses which converge in a focus region, extreme pressure differences are generated, which leads to destruction of the cellular structure. This is attributable to the formation and destruction of cavitation bubbles in liquids in the tissue, which are created by the pressure differences. In histotripsy, the pulse parameters for generating the ultrasonic pulses, (e.g., the pulse duration, pulse amplitude, or pause times between individual ultrasonic pulses or between sequences of ultrasonic pulses), are selected such that a high energy input occurs which leads to the severe expansion and finally destruction of the cavitation bubbles, but without causing significant heat generation. The bursting of the cavitation bubbles is accompanied by shock waves and correspondingly large forces on surrounding tissue, which leads to the destruction of the cell structure. This may be designated destructive cavitation.

However, according to the selection of the pulse parameters, it is also possible to generate the cavitation bubbles and, if appropriate, to maintain them stably without destroying them by further energy input. This may be designated non-destructive cavitation.

SUMMARY AND DESCRIPTION

It is an object of the present disclosure, in the therapeutic ultrasonic treatment of a tissue region which contains a flowing liquid, to reduce the risk of undesirable damage to healthy tissue.

This object is achieved by way of a therapeutic apparatus as disclosed herein.

The scope of the present disclosure is defined solely by the appended claims and is not affected to any degree by the statements within this summary. The present embodiments may obviate one or more of the drawbacks or limitations in the related art.

The disclosure is based upon the concept of determining the flow velocity of the liquid and of moving the focus region of radiated-in ultrasonic pulses along with the flowing liquid so that an energy input is selectively greatest where the flow velocity matches the movement velocity of the focus region.

According to one aspect, a therapeutic apparatus is provided for therapeutic ultrasonic treatment of a tissue region that contains a flowing liquid. The therapeutic apparatus has at least one ultrasonic source and at least one control unit. The at least one control unit is configured to activate the at least one ultrasonic source according to a pulse parameter set so that the at least one ultrasonic source radiates ultrasonic pulses for therapeutic ultrasonic treatment into the tissue region, in particular if the at least one ultrasonic source is accordingly positioned relative to the tissue region. The therapeutic apparatus has a measuring system configured to determine a flow velocity of the liquid. The therapeutic apparatus has a focus control system configured to move a focus region of the ultrasonic pulses dependent upon the determined flow velocity relative to the tissue region over a longitudinal portion so that a movement direction of the movement of the focus region relative to the tissue region corresponds to a flow direction of the liquid and a movement velocity of the movement of the focus region corresponds to the flow velocity.

In particular, the measuring system is also configured to determine the flow direction of the liquid.

The fact that the focus region is moved over the longitudinal portion may be understood in particular in that the focus region is moved parallel to the flow of the liquid over a particular path. The movement may therein be straight, but if required, may also be curved.

The pulse parameter set has corresponding values for at least one predetermined pulse parameter. The at least one pulse parameter may include, for example, a pulse duration of the ultrasonic pulses, a pulse amplitude of the ultrasonic pulses, a pause time between successive ultrasonic pulses or between associated sequences of successive ultrasonic pulses, a duty cycle of the ultrasonic pulses, and so on.

By way of the setting of the at least one pulse parameter, the strength of the pressure differences generated in the tissue by the ultrasonic pulses, in particular in the focus region, may be set. The pulse parameter set may be understood as quantifying an effective energy or the effective power introduced by the ultrasonic pulses, possibly time-dependently. In this way, by setting the at least one pulse parameter, in particular a rate for generating cavitation bubbles may be adapted and at the same time, the size of the cavitation bubbles generated may be controlled. Consequently, by setting the at least one pulse parameter, it may be controlled whether and under which conditions a destructive cavitation occurs.

The at least one control unit may include one or more computing units, drivers, and/or switching circuits.

In order to generate the ultrasonic pulses, the at least one control unit may set the parameter values of the pulse parameter set such that by way of the ultrasonic pulses radiated in, cavitation bubbles may be generated in the liquid. If a further energy input by way of the ultrasonic pulses takes place or if further ultrasonic pulses are radiated in, the cavitation bubbles may be destroyed and a destructive cavitation then takes place. By way of the destruction of the cavitation bubbles, large forces may be generated on surrounding tissue which may thereby be destroyed and this may correspond to a desired therapeutic effect.

The at least one control unit may set the parameter values of the pulse parameter set, in particular, such that the destructive cavitation occurs in the liquid if the liquid does not move or substantially does not move relative to the focus region or, in other words, if the focus region therefore moves rapidly in the same direction as the liquid. If, however, a significant relative movement of the liquid in relation to the focus region takes place, then the energy introduced into a particular liquid volume is lower because an irradiation then only takes place for a shorter time. The greater the velocity of the liquid relative to the focus region, the lower is the energy introduced into the volume of liquid. Accordingly, the at least one control unit may set the parameter values of the pulse parameter set, in particular, so that a destructive cavitation only occurs if the velocity of the liquid relative to the focus region is equal to zero or lies within a predetermined tolerance range around zero.

The therapeutic apparatus thus enables a locally selective destructive cavitation to be generated so that tissue is destroyed only in the region of substantially matching velocities of the liquid and the focus region, but not outside of this region.

The movement of the focus region may also take place, in particular, repeatedly or cyclically, so that the focus region is moved multiple times along the same longitudinal portion in order to achieve a more effective influence on the tissue.

The tissue may contain not just solid, but also liquid tissue, such as blood or lymph or cellular fluid, in particular. The tissue region may be a vessel, e.g., a blood vessel or a part of a vessel, and the liquid may be a liquid flowing in the interior of the vessel, e.g., blood.

The flow velocity in the vessel is not necessarily spatially constant and, in particular, is not spatially constant if a vessel constriction, also called a stenosis, is present. In this event, the flow velocity in the region of the stenosis is increased as compared with portions before and after the stenosis.

Alternatively, or in addition, to the spatial variability, the flow velocity may also vary temporally, for example, with a cardiac phase or a cardiac cycle. It is therefore also possible to undertake the ultrasonic irradiation adapted and/or timed to one or more cardiac phases of a cardiac cycle.

The at least one control unit may therefore set the parameter values of the pulse parameter set such that in the region of the stenosis, a destructive cavitation occurs which may lead to a destruction of the tissue creating the stenosis. Further removed from the stenosis and on the vessel walls and/or outside the vessel, tissue damage may not occur due to the selectivity described above.

In one example, the focus region of the ultrasonic pulses may be punctiform. In reality, however, this has a finite extent so that the focus region may be described, at least approximately, by a three-dimensional geometric figure. The center of the focus region may lie, for example, in the center of gravity of the geometric figure. For example, the focus region may be described approximately by a sphere, an ellipsoid or an ovoid. The center of the focus region is positioned, in particular, in the region of the flowing liquid, therefore in the case of a vessel, in the interior of the vessel.

The shape and/or extent of the focus region may be exactly defined in some embodiments by, for example simultaneous, emission of further ultrasonic pulses of opposing polarity, the further focus regions of which adjoin the focus region, possibly more exactly defined and/or enhanced to a certain extent.

The measuring system contains, dependent upon the embodiment, for example, a sensor system and a measurement control unit for evaluating measurement values or images or image sequences obtained by the sensor system, in order to determine the flow velocity.

The therapeutic apparatus has, for example, a histotripsy apparatus or is configured as a histotripsy apparatus which contains the at least one ultrasonic source. The at least one ultrasonic source is then configured, in particular, as at least one histotripsy transducer.

In order to move the focus region relative to the tissue region, the tissue region and/or a patient support or suchlike may be moved in a static coordinate system, for example, a substrate on which the therapeutic apparatus is situated, for example, robotically moved while the at least one ultrasonic source remains unmoving in the reference coordinate system or the at least one ultrasonic source may be moved in the reference coordinate system while the tissue region remains unmoved. A combination of both movements is also conceivable.

The focus control system then contains, for example, corresponding actuators, motors, robots, and/or other drive components for moving the at least one ultrasonic source and/or the tissue region, and a focus control unit for activating the aforementioned components. The focusing unit may therein also be part of the at least one control unit.

For example, a housing with a gel cushion may be positioned on a patient surface. A robot may move the at least one ultrasonic source on the patient surface mechanically, so that the focus region is also moved as described. The focus region may therein be electronically adapted along a longitudinal axis.

In certain embodiments, however, neither the at least one ultrasonic source nor the tissue region is moved in the reference coordinate system. Rather, the at least one ultrasonic source may be activated by an activation electronics system such that the position of the focus region may be changed in a targeted manner by overlaying ultrasonic waves of different phase positions. Such ultrasonic sources may also be designated phase-controlled array transducers or phased-array transducers. The focusing system therein contains the activation electronics system or consists thereof. The activation electronics system may therein also be part of the at least one control unit.

According to at least one embodiment of the therapeutic apparatus, the focus control system is configured to control the movement of the focus region by way of electronic control of the at least one ultrasonic source, wherein during the movement of the focus region relative to the tissue region, a position and an orientation of the at least one ultrasonic source relative to the tissue region are unchanged.

According to at least one embodiment, the at least one ultrasonic source includes at least one phased-array transducer and the focusing system, in particular, the activation electronics system is configured to control the movement of the focus region by way of phase control of the at least one phased-array transducer.

Advantageously, the focus region may thereby be moved very exactly and with very high velocities because no mechanical components are moved.

According to at least one embodiment, the at least one phased-array transducer includes at least one annular phased-array transducer or as at least one curved phased-array transducer.

In alternative embodiments, the at least one ultrasonic source may have a plurality of ultrasonic transducers or ultrasonic transducer arrays which each have a corresponding focus region in the tissue region.

The ultrasonic transducers or ultrasonic transducer arrays may then be activated sequentially so that the individual focus regions are switched on sequentially according to the flow velocity.

In some embodiments, a plurality of focus regions may also be moved simultaneously along the longitudinal portion so that, in particular, a chain or a train of focus regions is moved along the longitudinal portion. By this process, the treatment duration may be reduced.

Two or more of the variants described with regard to the movement of the focus region may also be combined in different embodiments. Thus, for example, limitations which would be caused by a purely mechanical or a purely electronic control, for example, with regard to the possible movement amplitude or movement velocity may be overcome.

According to at least one embodiment of the therapeutic apparatus, the measuring system is configured as a Doppler sonography system.

The measuring system thus has at least one ultrasonic transducer and a measuring control unit which may be, for example, part of the at least one control unit which may activate the at least one ultrasonic transducer for imaging according to Doppler sonography. The measuring control unit or the at least one control unit is configured, on the basis of a result of the imaging, to determine the flow velocity and, for example, also the flow direction of the liquid.

The at least one ultrasonic source for generating the ultrasonic pulses for therapeutic ultrasonic treatment may be, in principle, independent of the at least one ultrasonic transducer of the measuring system.

According to at least one embodiment, the measuring system is thus configured to determine on a position-dependent basis the flow velocity along the flow direction. The focus control system is configured to control the movement of the focus region so that the movement velocity of the movement of the focus region corresponds to a maximum flow velocity of the flow velocity determined on a position-dependent basis.

It may thus be achieved that the maximum energy input takes place where the maximum flow velocity arises. In the example of a vessel constriction, therefore the region of the vessel constriction is treated, whereas surrounding regions may remain substantially unaffected.

In particular, the region of the maximum flow velocity appears stationary relative to the focus region, whereas the surrounding regions with lower flow velocity have a movement relative to the focus region.

According to at least one embodiment, the focus control system is configured to control the movement of the focus region such that the focus region is moved along the flow direction via the longitudinal portion, wherein in a first part of the longitudinal portion, the maximum flow velocity prevails and in a second part of the longitudinal portion, a flow velocity prevails that is lower than the maximum flow velocity.

For example, the first part may be the specific region of the vessel constriction and the second part is a region of the vessel in which no or a less severe constriction is present.

The focus region is then moved with a constant velocity which corresponds to the maximum flow velocity along the first and the second part of the longitudinal portion. The at least one control unit may therein specify the parameter set such that in the first part, but not in the second part, destructive cavitation takes place.

According to at least one embodiment, the at least one control unit is configured to determine the pulse parameter set dependent upon the flow velocity, in particular the flow velocity determined on a location-dependent basis such that by way of the ultrasonic pulses radiated in, a destructive cavitation is caused in the first part of the longitudinal portion and in the second part of the longitudinal portion, no destructive cavitation is caused. For example, in the second part of the longitudinal portion, a non-destructive cavitation may be caused.

According to at least one embodiment, the measuring system is configured to determine a further flow velocity of the cavitation bubbles that are created by the non-destructive cavitation and to determine the flow velocity of the liquid on the basis of the further flow velocity of the cavitation bubbles.

For this purpose, the measuring system may have an imaging modality, for example, an ultrasound-based imaging modality, an X-ray based imaging modality or a magnetic resonance tomography system which may represent the movement of the cavitation bubbles and thereby their velocity. Because the cavitation bubbles move with the flowing liquid, it may be assumed, in particular, that the flow velocity of the liquid corresponds to the flow velocity of the cavitation bubbles.

According to at least one embodiment, the measuring system is configured to determine a temporal change of the flow velocity, in particular the maximum flow velocity. The focus control system is configured to control the movement of the focus region so that the focus region is moved repeatedly and/or cyclically along the longitudinal portion, and to adapt the movement velocity of the movement of the focus region to the flow velocity according to the change in the flow velocity.

Therein the movement velocity of the movement of the focus region may remain constant, for example, during a cycle and, where a change in the flow velocity has been established, the movement velocity may be adapted in the following cycle. Alternatively, the movement velocity of the movement of the focus region may remain constant during a group with a predetermined number of cycles and, where a change in the flow velocity has been established, the flow velocity may be adapted in the following group of cycles.

According to a further aspect, a computer program with commands is provided. On execution of the commands by a therapeutic apparatus, in particular by way of the at least one control unit of the therapeutic apparatus, the commands cause the therapeutic apparatus to carry out a method for therapeutic ultrasonic treatment.

According to the method for therapeutic ultrasonic treatment, ultrasonic pulses are radiated into the tissue region for therapeutic ultrasonic treatment and a flow velocity of the liquid is determined. The focus region of the ultrasonic pulses is moved relative to the tissue region over a longitudinal portion dependent upon the determined flow velocity, wherein a movement direction of the movement of the focus region corresponds to a flow direction of the liquid and a movement velocity of the movement of the focus region corresponds to the flow velocity.

The method for therapeutic ultrasonic treatment may be a method for ultrasonic treatment of a vessel constriction, wherein the tissue region corresponds to a vessel which has the vessel constriction. The focus region may be moved in the interior of the vessel.

Further embodiments of the method and thus of the computer program follow directly from the different embodiments of the therapeutic apparatus and vice versa. In particular, individual features and corresponding explanations relating to the different embodiments of the therapeutic apparatus according to the improved concept may be transferred analogously to corresponding embodiments of the computer program.

According to a further aspect, a computer-readable storage medium is also provided which stores a computer program.

A computer program and a computer-readable storage medium may refer to a respective computer program products with the commands.

Where, in the context of the present disclosure, a component of the therapeutic apparatus, (e.g., the at least one control unit or the focus control system of the therapeutic apparatus), is designed, configured, arranged, or suchlike, to carry out or realize a particular function, to achieve a particular effect or to serve a particular purpose. This may be understood as meaning that the component, beyond the fundamental or theoretical usability or suitability of the components for this function, effect, or purpose, by way of a corresponding adaptation, programming, physical design, and suchlike, is actually and specifically capable of carrying out or realizing the function, achieving the effect, or serving the purpose.

A computing unit may be understood to be, in particular, a data processing device which contains a processing circuit. The computing unit may thus, in particular, process data to carry out computation operations. This also includes, where relevant, operations to carry out indicated access operations to a data structure, for example, a look-up table (LUT).

The computing unit may contain, in particular, one or more computers, one or more microcontrollers and/or one or more integrated circuits, for example, one or more application-specific integrated circuits (ASICs), one or more field-programmable gate arrays (FPGAs), and/or one or more single chip systems (system on a chip, SoC). The computing unit may also contain one or more processors, for example, one or more microprocessors, one or more central processing units (CPUs), one or more graphics processing units (GPUs) and/or one or more signal processors, in particular one or more digital signal processors (DSPs). The computing unit may also contain a virtual network of computers or others of the aforementioned units.

In different exemplary embodiments, the computing unit contains one or more hardware and/or software interfaces and/or one or more storage units.

A storage unit may be configured as a volatile data store, for example, a dynamic random access memory (DRAM) or as a static random access memory (SRAM) or as a non-volatile data store, for example, a read-only memory (ROM), as a programmable read-only memory (PROM), as an erasable read-only memory (EPROM), as an electrically erasable read-only memory (EEPROM), as a flash memory or flash-EEPROM, as a ferroelectric random access memory (FRAM), as a magnetoresistive random access memory (MRAM), or as a phase-change random access memory (PCRAM).

Further features are disclosed in the claims, the drawings, and the description of the drawings. The features and combinations of features mentioned in the description above and the following features and combinations of features mentioned in the description of the drawings and/or shown in the drawings alone may be included by the disclosure not only in the respective combinations given, but also in other combinations. In particular, embodiments and combinations of features which do not have all the features of an originally formulated independent claim are also included by the disclosure. Furthermore, embodiments and combinations of features which go beyond or deviate from the combinations of features represented by the references in the claims are included by the disclosure.

The disclosure is now described in greater detail by reference to actual exemplary embodiments and the associated schematic drawings. In the figures, the same or functionally equivalent elements have been given the same reference characters. The description of the same or functionally equivalent elements will, where relevant, not necessarily be repeated in relation to different figures.

DETAILED DESCRIPTION

Figure 1:
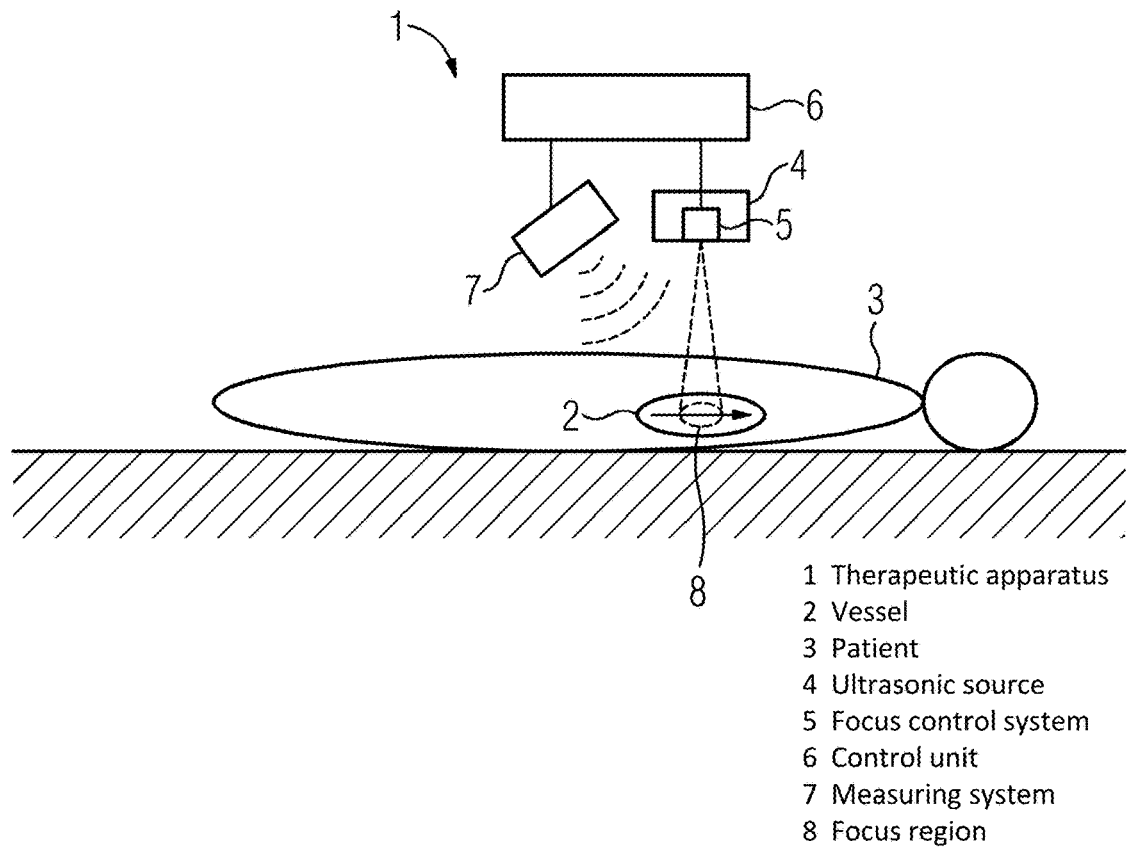
FIG. 1 depicts a schematic representation of an exemplary embodiment in a therapeutic apparatus.
Figure 2:
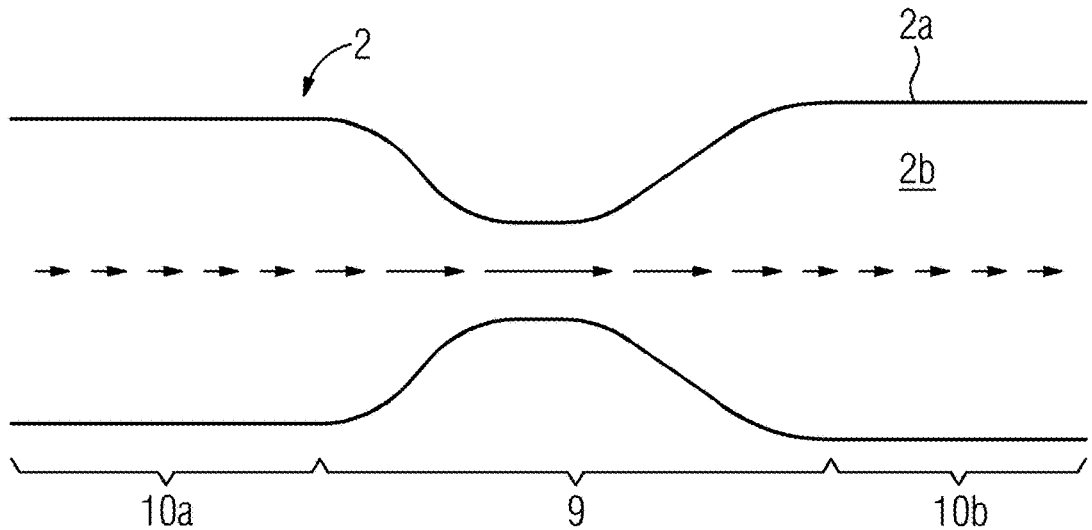
FIG. 2 depicts a schematic representation of an example of a tissue region.

FIG. 1 shows schematically an exemplary embodiment of a therapeutic apparatus 1. Furthermore, a patient 3 and a tissue region of the patient 3, for example, a vessel 2 with a vessel wall 2a and a liquid 2b, in particular blood, flowing in the interior of the vessel is shown schematically. The vessel 2 is shown again schematically in FIG. 2.

The therapeutic apparatus 1 has one or more ultrasonic sources 4 and a control unit 6 configured to activate the ultrasonic sources 4 according to a pulse parameter set in order to radiate ultrasonic pulses into the vessel 2 for therapeutic ultrasonic treatment, so that, in particular, a focus region 8 of the ultrasonic pulses is also situated within the vessel 2. The extent of the focus region 8 may therein be larger than a vessel cross-section so that, for example, the focus region 8 overlaps with the vessel 2.

The therapeutic apparatus 1 has a measuring system 7, in particular a Doppler sonography system which may be controlled by the control unit 6. By this, the control unit 6 may determine a flow velocity of the liquid 2b in a position-dependent manner. If relevant, a separate measuring control unit (not shown) may also be provided for determining the flow velocity and/or for activating the measuring system 7.

The ultrasonic sources 4 are configured, for example, as phased-array transducers so that a focus control system 5 may control the position of the focus region 8 electronically, without the ultrasonic sources 4 themselves having to be moved. The focus control system 5 is configured to move the focus region 8 of the ultrasonic pulses relative to the vessel 2 parallel to the flow of the liquid 2b, wherein a movement velocity of the movement of the focus region 8 corresponds to the maximum flow velocity of the liquid 2b.

If the vessel 2 has, for example, a vessel constriction 9, the velocity of the liquid 2b in the region of the vessel constriction 9 is a maximum and in the adjacent regions 10a, 10b before and after the vessel constriction 9, it is lower.

The focus region 8 may thus be moved along the region 10a of the vessel constriction 9 and the region 10b with the maximum flow velocity. In the region of the vessel constriction 9, the relative velocity of the focus region 8 in relation to the liquid 2b is therefore equal to zero or approximately zero, whereas the relative velocity in the regions 10a, 10b is greater.

Thereby, destructive cavitation may be generated for histotripsy selectively and/or resonantly at the position of the vessel constriction 9. As a result of the bubble collapse in the liquid 2b in the region of the vessel constriction 9, sufficient energy is generated gradually to ablate the wall regions of the vessel walls of the vessel constriction 9. In the regions 10a, 10b cavitation bubbles that are possibly created move away from the focus region 8 so that an efficient multipulse excitation and collapsing of the cavitation bubbles does not take place.

Herein, the fact is made use of that the destructive cavitation is triggered, in the context of histotripsy, by a sequence of a plurality of strongly focused pulses, wherein one pulse alone causes no, or only slight, tissue damage. The excitation of the same tissue volume element or liquid volume element by the whole pulse sequence results in an efficient tissue destruction by histotripsy. Examples of use are, for instance, shock-scattering histotripsy or boiling histotripsy.

If the focus region is not moved at the flow velocity, an insufficient energy input for destructive cavitation may occur because a relative movement occurs between the liquid and the focus region. In one example, due to the movement adapted to the flow velocity of the focus region, the liquid and the focus region are static relative to one another, so that a destructive cavitation may be achieved.

Phase effects may therein lead, in particular, to an increased selectivity. If moved structures are resonantly excited with the correspondingly optimized ultrasonic phase position, the bubble formation is enhanced again here. Conversely, a non-phase-optimized excitation may be significantly less efficient where there is resonant energy input into the bubble cloud.

Making use of Doppler sonography, the flow velocity and the flow direction of the liquid 2b in the region of the vessel constriction 9 may be monitored and the movement of the focus region 8 as described may be dynamically adapted.

For example, if the vessel constriction 9 has changed its shape by way of the treatment, the change thereby caused to the flow velocity may thus be adjusted. The adaptation of the flow velocity to the pulse cycle is thus possible, for instance by gating at the maximum flow velocity within a pulse cycle and/or by way of continual adaptation of the pulse parameters.

In summary, a high degree of selectivity and safety in the treatment of tissue regions, particularly vessel stenoses, by histotripsy is enabled. Damage to healthy tissue may be prevented or reduced.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A therapeutic apparatus for therapeutic ultrasonic treatment of a tissue region having a flowing liquid, the therapeutic apparatus comprising:
   at least one ultrasonic source; and
   at least one controller configured to activate the at least one ultrasonic source according to a pulse parameter set in order to radiate ultrasonic pulses into the tissue region for the therapeutic ultrasonic treatment,
   wherein the therapeutic apparatus is configured to determine a flow velocity of the flowing liquid,
   wherein the therapeutic apparatus is further configured to move a focus region of the ultrasonic pulses relative to the tissue region over a longitudinal portion to provide a movement of the focus region, and
   wherein a movement direction of the movement of the focus region corresponds to a flow direction of the flowing liquid and a movement velocity of the movement of the focus region corresponds to the flow velocity.

2. The therapeutic apparatus of claim 1, wherein the therapeutic apparatus comprises a Doppler sonography system.

3. The therapeutic apparatus of claim 1, wherein the therapeutic apparatus is further configured to:
   determine, on a position-dependent basis, the flow velocity along the flow direction, and
   control the movement of the focus region so that the movement velocity corresponds to a maximum flow velocity of the flow velocity determined on the position-dependent basis.

4. The therapeutic apparatus of claim 3, wherein the therapeutic apparatus is further configured to control the movement of the focus region so that the focus region is moved along the flow direction via the longitudinal portion,
   wherein, in a first part of the longitudinal portion, the maximum flow velocity prevails, and
   wherein, in a second part of the longitudinal portion, a lower flow velocity prevails that is lower than the maximum flow velocity.

5. The therapeutic apparatus of claim 4, wherein the at least one controller is further configured to determine the pulse parameter set dependent upon the flow velocity such that, by way of the ultrasonic pulses radiated in, a destructive cavitation is caused in the first part of the longitudinal portion and non-destructive cavitation is caused in the second part of the longitudinal portion.

6. The therapeutic apparatus of claim 4, wherein the at least one controller is further configured to determine the pulse parameter set dependent upon the flow velocity such that, by way of the ultrasonic pulses radiated in, a non-destructive cavitation is caused in the second part of the longitudinal portion.

7. The therapeutic apparatus of claim 6, wherein the therapeutic apparatus is further configured to:
   determine a further flow velocity of cavitation bubbles that are created by the non-destructive cavitation in the second part of the longitudinal portion, and
   determine the flow velocity of the flowing liquid based on the further flow velocity of the cavitation bubbles.

8. The therapeutic apparatus of claim 1, wherein the therapeutic apparatus is further configured to:
   establish a change in the flow velocity, control the movement of the focus region so that the focus region so that the focus region is moved repeatedly along the longitudinal portion, and adapt the movement velocity of the movement of the focus region to the flow velocity according to the change in the flow velocity.

9. The therapeutic apparatus of claim 1, wherein the therapeutic apparatus comprises a histotripsy apparatus containing the at least one ultrasonic source.

10. The therapeutic apparatus of claim 1, wherein the therapeutic apparatus is further configured to control the movement of the focus region by way of electronic control of the at least one ultrasonic source, and wherein, during the movement of the focus region relative to the tissue region, a position and an orientation of the at least one ultrasonic source relative to the tissue region are unchanged.

11. The therapeutic apparatus of claim 1, wherein the at least one ultrasonic source comprises at least one phased-array transducer, and wherein the therapeutic apparatus is further configured to control the movement of the focus region by way of phase control of the at least one phased-array transducer.

12. The therapeutic apparatus of claim 11, wherein the at least one phased-array transducer comprises at least one annular phased-array transducer or at least one curved phased-array transducer.

13. A non-transitory computer program product with commands which, when executed by a therapeutic apparatus, cause the therapeutic apparatus to:

activate, by a controller of the therapeutic apparatus, at least one ultrasonic source according to a pulse parameter set in order to radiate ultrasonic pulses for therapeutic ultrasonic treatment into a tissue region having a flowing liquid;

determine a flow velocity of the flowing liquid by the therapeutic apparatus; and move, by the therapeutic apparatus, a focus region of the ultrasonic pulses relative to the tissue region over a longitudinal portion dependent upon the determined flow velocity to provide a movement of the focus region, wherein a movement direction of the movement of the focus region corresponds to a flow direction of the flowing liquid and a movement velocity of the movement of the focus region corresponds to the flow velocity.

14. The non-transitory computer program product of claim 13, wherein the commands, when executed by the therapeutic apparatus, cause the therapeutic apparatus to provide an ultrasonic treatment of a vessel constriction, and wherein the tissue region corresponds to a vessel having the vessel constriction.

* * * * *